United States Patent [19]

Fischer et al.

[11] 4,239,706

[45] Dec. 16, 1980

[54] PREPARATION OF CROTONALDEHYDES

[75] Inventors: Rolf Fischer, Heidelberg; Hans-Martin Weitz, Bad Durkheim, both of Fed. Rep. of Germany

[73] Assignee: BASF Aktiengesellschaft, Fed. Rep. of Germany

[21] Appl. No.: 20,458

[22] Filed: Mar. 14, 1979

[30] Foreign Application Priority Data

Apr. 11, 1978 [DE]  Fed. Rep. of Germany ....... 2815539

[51] Int. Cl.$^3$ ............................................. C07C 47/21
[52] U.S. Cl. ................................................. 568/484
[58] Field of Search ........................ 260/601 R, 603 R

[56] References Cited

U.S. PATENT DOCUMENTS

| | | | |
|---|---|---|---|
| 2,616,887 | 11/1952 | Danzig et al. | 526/84 |
| 2,920,081 | 1/1960 | Privette | 260/601 R |
| 3,317,593 | 5/1967 | Enk et al. | 260/601 R |
| 3,639,472 | 2/1972 | Sennewald et al. | 260/601 R |
| 3,780,194 | 12/1973 | Acton et al. | 426/548 |
| 3,899,539 | 8/1975 | Fernholz et al. | 260/601 R |

FOREIGN PATENT DOCUMENTS

| | | |
|---|---|---|
| 2062950 | 7/1970 | Fed. Rep. of Germany . |
| 2417658 | 10/1975 | Fed. Rep. of Germany . |
| 1494430 | 12/1977 | United Kingdom . |

OTHER PUBLICATIONS

Journal fur Praktische Chemie, vol. 155 (1940), pp. 311–316.
Agricultural Biological Chemistry, vol. 39 (1975), pp. 2431–2432.
Annalen der chem es, vol. 494 (1932), pp. 263, 272–273.
Jour. Amer. Chem. Society, vol. 54 (1932), pp. 4385–4391.
Methoden der Organischen Chemie, vol. VI/3 (1965), pp. 592–594.
Ullmanns Encyklopadie der technischen Chemie, vol. 5 (1954), p. 616.

*Primary Examiner*—Werren B. Lone
*Attorney, Agent, or Firm*—Keil & Witherspoon

[57] ABSTRACT

Crotonaldehydes are prepared by reacting 1,4-diacyloxy-but-2-enes with water in the presence of a cation exchanger. The products are starting materials for the preparation of dyes, crop protection agents, polymerization inhibitors and vulcanization accelerators.

6 Claims, No Drawings

PREPARATION OF CROTONALDEHYDES

The present invention relates to a process for the preparation of crotonaldehydes by reacting 1,4-diacyloxy-but-2-enes with water in the presence of a cation exchanger.

It is known that tiglic aldehyde (2-methylcrotonaldehyde) can be prepared by condensing acetaldehyde and propionaldehyde under carbon dioxide in the presence of sodium hydroxide solution, the yield being 30 percent (Journal für praktische Chemie, 155, (1940), 315–316), by reacting 3,4-epoxy-3-methyl-but-1-ene with palladium acetylacetonate and triphenylphosphine, the yield being 26–60 percent (Agricultural Biological Chemistry, 39 (1975), 2,431–2,432), or by isomerizing 2-ethylacrolein with calcium chloride and distilling the product (Liebigs Annalen der Chemie, 494 (1932), 273).

An article in Journal of the American Chemical Society, 54 (1932), 4,390, discloses that tiglic aldehyde can be obtained by heating 2-methyl-but-2-ene-1,4-diol diacetate in a solution of hydrogen chloride in methyl alcohol, and describes further syntheses using the un-esterified diol, by reacting the latter in the presence of anhydrous zinc chloride and distilling the product, or by heating the diol in the presence or absence of hydrogen chloride. All these reactions were carried out with relatively small amounts, for example with 4 grams of diol. The article expressly points out that when reacting larger amounts, namely 40–50 grams, the un-esterified diol is used as the starting material and is reacted at 0° C. with aqueous 11 N hydrochloric acid for more than 2 hours. Pyridine is then added and only at that stage is the mixture heated cautiously, the aqueous phase separated off and distilled, and the isolated crude tiglic aldehyde subjected to steam distillation from a slightly acid solution, dried and again fractionated. A yield of 65 percent is obtained. This embodiment is regarded as the most advantageous where fairly large batches are concerned. A particular disadvantage of the process is that the diol is used as the starting material and that equimolar amounts of acid are used, which subsequently have to be neutralized again with pyridine. Thus, substantial amounts of salt are formed, and this constitutes a disadvantage. In addition, residual pyridine must subsequently be removed by steam distillation.

All these processes are unsatisfactory in respect of simplicity and economy of operation, yield, space-time yield, working-up and purity of the end product.

We have found that a crotonaldehyde of the formula

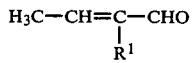

where $R^1$ is hydrogen or an aliphatic radical, is obtained in an advantageous manner when a 1,4-diacyloxy-but-2-ene of the formula

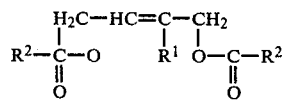

where $R^1$ has the above meanings and $R^2$ is hydrogen or an aliphatic radical, is reacted with water in the presence of a cation exchanger.

Where 2-methyl-1,4-diacetoxy-but-2-ene is used, the reaction can be represented by the following equation:

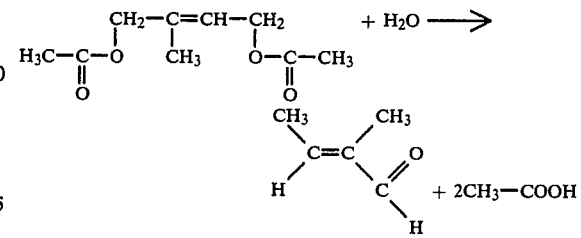

Compared to the conventional processes, the process according to the invention surprisingly gives crotonaldehydes, and in particular tiglic aldehyde, more simply and more economically, and in better yield and higher purity. Working-up is simple, and expensive or difficult-to-obtain reactants are not needed. It is particularly on an industrial scale that the process can be carried out advantageously. The starting material can be converted in a one-step reaction, and without prior conversion to the diol, to give a crotonaldehyde, especially tiglic aldehyde. Large amounts of salt resulting from neutralization are avoided. All these advantages of the process according to the invention are surprising since, particularly in view of the use of the diester as the starting material, a substantially poorer yield would have been expected in the light of the prior art.

It was also not possible to foresee how 1,4-diacetoxy-but-2-enes and especially 2-methyl-1,4-diacetoxy-but-2-ene and/or the corresponding diols resulting from hydrolysis of the above compounds would react further in the presence of water and a cation exchanger. According to Houben-Weyl, Methoden der Organischen Chemie, Volume 6/3, pages 592–594, dihydrofurans are formed from 1,4-dihydroxyalk-2-enes in the presence of acidic catalysts. For example, but-2-ene-1,4-diol reacts with hydrogen chloride or sulfuric acid to give 2,5-dihydrofuran, and hex-3-ene-2,5-diol reacts with hydrogen chloride to give 2,5-dimethyl-2,5-dihydrofuran. German Laid-Open Application DOS 2,062,950 describes the conversion of cis-but-2-ene-1,4-diol monoacetate or diacetate to 2,5-dihydrofuran in the presence of acids.

The starting materials, for example 2-methyl-1,4-diacetoxy-but-2-ene, can be prepared, starting, for example, from isoprene, either via compounds such as 2-methyl-1,4-dibromo-but-2-ene, which are then reacted with the alkali metal salts of the appropriate carboxylic acids (Journal of the American Chemical Society, 54 (1932), 4,388) or more advantageously in a one-step olefin acyloxylation, for example the acetoxylation of isoprene with acetic acid and oxygen in the presence of platinum containing tellurium, in accordance with the process described in German Laid-Open Application DOS 2,417,658. Preferred starting materials II and accordingly preferred end products I are those where the individual radicals $R^1$ and $R^2$ are identical or different and each is hydrogen or alkyl of 1 to 7 carbon atoms. Particularly preferred compounds are those where $R^1$ and/or $R^2$ is methyl. The above radicals may in addition be substituted by groups which are inert under the reaction conditions, eg. alkyl of 1 to 4 carbon atoms. It is also possible to use, in place of starting materials II, compounds which form the starting materials II under the reaction conditions, for example but-1-ene-3,4-diol diesters, 2-methyl-but-1-ene-3,4-diol diesters and 3-methyl-but-1-ene-3,4-diol diesters. Examples of suitable starting materials II or esters forming starting materials II under the reaction conditions are the diesters of but-2-ene-1,4-diol, but-1-ene-3,4-diol, 2-methyl-but-2-ene-1,4-diol, 2-methyl-but-1-ene-3,4-diol and 3-methyl-but-1-ene-3,4-diol with formic acid, propionic acid, butyric acid, isobutyric acid, valeric acid, isovaleric acid, caproic acid, enanthic acid and especially acetic acid, and diesters of the 2-ethyl-, 2-propyl-, 2-isopropyl-, 2-butyl-, 2-isobutyl-, 2-sec.-butyl-, 2-tert.-butyl-, 2-pentyl-, 2-isopentyl- and 2-hexyl-1,4-diol homologs.

The reaction is in general carried out at from 0° to 200° C., preferably from 80° to 120° C., under atmospheric or superatmospheric pressure, batchwise or continuously, in the presence of water. The amount of water is advantageously from 1 to 50, especially from 2 to 20, moles per mole of starting material II. In addition, organic solvents which are inert under the reaction conditions can be used. Suitable solvents are especially those which are miscible with water or have a high solvent power for water, for example alkanols and cycloalkanols, eg. ethanol, methanol, n-butanol, isobutanol, tert.-butanol, glycol, glycerol, sec.-butanol, n-propanol and isopropanol.

The reaction is carried out in the presence of acidic ion exchangers, namely cation exchangers, preferably acidic synthetic resin exchangers, advantageously in their acid form. Examples of such exchangers are all the cation exchangers described in Houben-Weyl, Methoden der Organischen Chemie, Volume I/1, page 528, Table 3. Preferably, exchangers of high and medium acidity are used, for example exchangers synthesized from styrene and divinylbenzene and containing sulfonic acid groups; strongly acidic inorganic cation exchangers, such as zeolites; polyphenolsulfonic acid resins, polystyrenesulfonic acid resins, polystyrenephosphonic acid resin, polystyrenephosphinic acid resins, or similar exchangers containing acidic resins, for example bifunctional condensation resins. For example, the above resins, commercially available under the registered trademarks ® Lewatit S 100, Amberlite IR-120, Lewasorb, Dowex 50 WX 8 and Amberlyst 15, may be used. The amount of the starting materials used and of the exchanger used depends on the selectivity or on the number of groups in the exchanger capable of undergoing exchange at the reaction temperature. In general, the amount of exchanger used is from 1 to 40 percent by weight, preferably from 5 to 25 percent by weight, based on starting material II. The amount of water contained in the dry exchanger, which may be up to 50 percent by weight, depending on the structure, is not included in the added water defined above. The shape and particle size of the exchanger can be chosen freely within a wide range. Regarding the preparation, and details of the use, of ion exchangers, reference may be made to the chapter on "Ionenaustauscher" in Houben-Weyl.

The reaction is carried out as follows: a mixture of starting material II, water and acidic cation exchanger, with or without organic solvent, is kept at the reaction temperature for from 0.5 to 24 hours. The end product is then isolated in the conventional manner, for example by filtration and fractional distillation of the filtrate. It is also possible, for example in the case of tiglic aldehyde, to distil the filtrate after further addition of water, in which case, if the distillation is carried out under atmospheric pressure, a two-phase mixture of tiglic aldehyde and water passes over at from about 80° to 100° C. and a single-phase mixture, consisting predominantly of water and acetic acid, passes over at from about 100° to 188° C. After separating the tiglic aldehyde and water phases, the former, which is already very pure, can, if required, be dried over a drying agent and again subjected to fractional distillation. Traces of carboxylic acids, eg. acetic acid, can be removed by neutralization. The tiglic aldehyde can be isolated particularly simply by distilling off, and condensing, a tiglic aldehyde/water mixture in an apparatus for continuously taking off the upper distillate phase of a two-phase mixture.

The crotonaldehydes obtainable by the process of the invention are valuable starting materials for the preparation of dyes, crop protection agents, polymerization inhibitors and vulcanization accelerators. Tiglic aldehyde can, for example, be used as an intermediate in the preparation of terpenes, or as a polymerization inhibitor in the manufacture of polyvinyl chloride (U.S. Patent 2,616,887). U.S. Patent 3,780,194 refers to the use of the syn.-oxime of tiglic aldehyde as a sweetener in foodstuffs. Regarding the use of the crotonaldehydes I, reference may in addition be made to the above publications and to Ullmanns Encyklopädie der technischen Chemie, Volume 5, page 616.

In the Examples which follow, parts are by weight and bear the same relation to parts by volume as that of the kilogram to the liter.

EXAMPLE 1

(a) 600 parts of glacial acetic acid and 15 parts of a catalyst containing palladium and tellurium (7.10 percent by weight of palladium and 1.19 percent by weight of tellurium on active charcoal) are heated to 95° C. in a reactor, after the apparatus has been flushed with nitrogen. In the course of 4 hours, 12,000 parts by volume of oxygen are introduced and at the same time 36.5 parts by weight of isoprene are added. After all has been added, nitrogen is passed through the reaction mixture at 95° C. for 30 minutes; the mixture is then allowed to cool and the catalyst is removed by filtering or centrifuging. The filtrate is subjected to fractional distillation. 61.8 parts of 2-methyl-1,4-diacetoxy-but-2-ene are obtained; boiling point 57°-59° C./0.3 mbar, $n_D^{20}=1.4478$.

(b) A polystyrenesulfonic acid resin cation exchanger commercially available under the registered trademark ®Dowex 50 WX 8 (50–100 mesh) is used; it is pretreated with hydrochloric acid and washed with water until the filtrate is neutral. A mixture of 100 parts of 2-methyl-1,4-diacetoxy-but-2-ene, 97 parts of water and 27 parts of cation exchanger is stirred for one hour under reflux. When the mixture has cooled, the ion exchanger is filtered off and the homogeneous filtrate is subjected to fractional distillation under atmospheric pressure. 38.3 parts of tiglic aldehyde (90% of theory, based on 2-methyl-1,4-diacetoxy-but-2-ene employed) are obtained; boiling point 116.5°–118° C./1,013 mbar; $n_D^{20}=1.4429$.

EXAMPLE 2

A polystyrenesulfonic acid resin cation exchanger commercially available under the registered trademark ®Lewatit SPC 118 H is used. A mixture of 100 parts of 2-methyl-1,4-diacetoxy-but-2-ene, 97 parts of water and 27 parts of the cation exchanger is reacted, and worked up, as described in Example 1. This gives 38.2 parts of tiglic aldehyde (84.6% of theory); boiling point 117°–118° C.

EXAMPLE 3

A polystyrenesulfonic acid resin cation exchanger commercially available under the registered trademark ®Dowex 50 WX 8 is used. A mixture of 100 parts of 2-methyl-1,4-diacetoxy-but-2-ene, 100 parts of water and 10.8 parts of the cation exchanger is stirred under reflux for 4 hours and worked up as described in Example 1. 39.2 parts of tiglic aldehyde (86.8% of theory) are obtained; boiling point 116°–119° C.

EXAMPLE 4

A polystyrenesulfonic acid resin cation exchanger commercially available under the registered trademark ®Amberlite IR-120 (20–50 mesh, water content 44–48 percent) is used.

A mixture of 119 parts of 2-methyl-1,4-diacetoxy-but-2-ene, 140 parts of water and 20 parts of the water-containing cation exchanger is heated for 2.5 hours at 95°–100° C. and at the same time the tiglic aldehyde is isolated by distilling off and condensing a tiglic aldehyde/water mixture in an apparatus for continuously taking off the upper distillate phase of a two-phase mixture. After having been dried with magnesium sulfate, the tiglic aldehyde is mixed with 3 parts of sodium carbonate. After filtration and subsequent distillation, 46.2 parts of tiglic aldehyde (85.9% of theory) are obtained; boiling point 116°–119° C., $n_D^{20} = 1.4455$.

We claim:

1. A process for the preparation of a crotonaldehyde of the formula

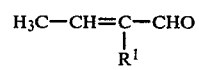

where $R_1$ is hydrogen or alkyl of 1-7 carbon atoms, wherein a 1,4-diacyloxy-but-2ene of the formula

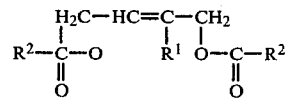

where $R^1$ has the above meanings and $R^2$ is hydrogen or alkyl of 1-7 carbon atoms, is reacted with water in the presence of a cation exchanger at a temperature of from 0° to 200° C.

2. A process as set forth in claim 1, wherein the reaction is carried out with from 1 to 50 moles of water per mole of starting material II.

3. A process as set forth in claim 1, wherein the reaction is carried out at from 80° to 120° C.

4. A process as set forth in claim 1, wherein the reaction is carried out with an exchanger which is synthesized from styrene and divinylbenzene and contains sulfonic acid groups, or with a zeolite, a polyphenolsulfonic acid resin, a polystyrenesulfonic acid resin, a polystyrenephosphonic acid resin, a polystyrenephosphinic acid resin or a bifunctional condensation resin.

5. A process as set forth in claim 1, wherein the reaction is carried out with an amount of exchanger of from 1 to 40 percent by weight, based on starting material II.

6. A process as set forth in claim 1, wherein $R^1$ and $R^2$ are methyl.

* * * * *